United States Patent [19]
Squyres et al.

[11] Patent Number: 5,464,981
[45] Date of Patent: Nov. 7, 1995

[54] METHODS OF SEPARATING SELECTED ITEMS FROM A MIXTURE INCLUDING RAISINS AND THE SELECTED ITEMS

[75] Inventors: Henry P. Squyres, Medford; Duncan B. Campbell, Central Point, both of Oreg.

[73] Assignee: Simco/Ramic Corporation, Medford, Oreg.

[21] Appl. No.: 386,329

[22] Filed: Feb. 10, 1995

Related U.S. Application Data

[63] Continuation of Ser. No. 237,736, May 3, 1994, abandoned, which is a continuation-in-part of Ser. No. 63,401, May 17, 1993.

[51] Int. Cl.$^6$ .................................................. B07C 5/342
[52] U.S. Cl. ...................... 250/341.8; 209/577; 209/587; 250/330
[58] Field of Search ................................ 250/910, 341.8, 250/330; 209/587, 577

[56] References Cited

U.S. PATENT DOCUMENTS

| 4,186,836 | 2/1980 | Wassmer et al. | 209/565 |
|---|---|---|---|
| 4,634,881 | 1/1987 | Billion | 250/572 |
| 4,723,659 | 2/1988 | Billion | 209/576 |
| 4,738,175 | 4/1988 | Little et al. | 83/76.8 |
| 5,085,325 | 2/1992 | Jones et al. | 209/580 |
| 5,134,291 | 7/1992 | Ruhl, Jr. et al. | 250/341 |
| 5,141,110 | 8/1992 | Trischan et al. | 209/524 |

FOREIGN PATENT DOCUMENTS

| 0247016 | 11/1987 | European Pat. Off. | 209/587 |
|---|---|---|---|
| 2430272 | 3/1980 | France | 209/587 |
| 1-301147 | 12/1989 | Japan | 250/910 |

OTHER PUBLICATIONS

Anzai, Yoshinori; Saikatsu, Takeo; Yamazaki, Hiroyoshi et al.; "*Rare–Gas Discharge Lamps Suitable For Industrial Use*"; Lighting Design and Application; Feb. 1987; pp. 33–38.

Wolfe, William L. and Zissis, George J., *The Infrared Handbook*, 1989, pp. 3–13, 3–121, 3–129, and 3–130.

McClure, Fred, "Theory of Near Infrared Reflectance Spectroscopy," instruction materials for FPEI/ASAE UV/VIS/NIR Measurement Fundamentals seminar, 1992, (three loose leaf sheets).

Primary Examiner—Constantine Hannaher
Attorney, Agent, or Firm—Stoel Rives Boley Jones & Grey

[57] ABSTRACT

Methods of operating an automated optical inspection system to separate selected items, e.g., grape stems (124, 126, 128), grape leaves (122), or rocks from a mixture (16) of those items and raisins (120) include illuminating the mixture with illumination (37', 37") characterized by a spectral power distribution (86, 98) in the near infrared (88, 90, 100, 102), detecting reflections of wavelengths of the illumination in the near infrared, identifying the selected items based on the detected reflections, and sorting the selected items from the mixture.

27 Claims, 4 Drawing Sheets

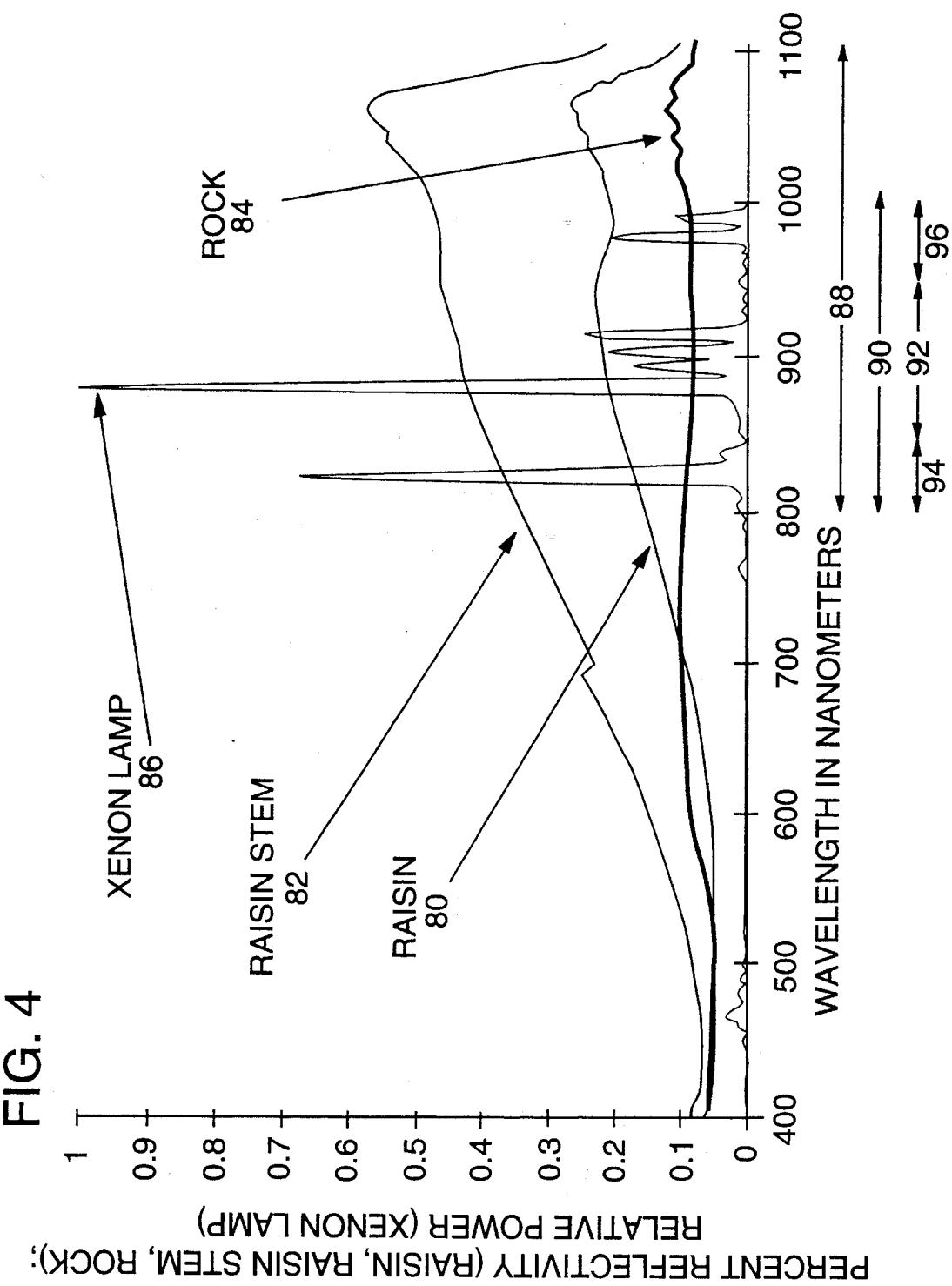

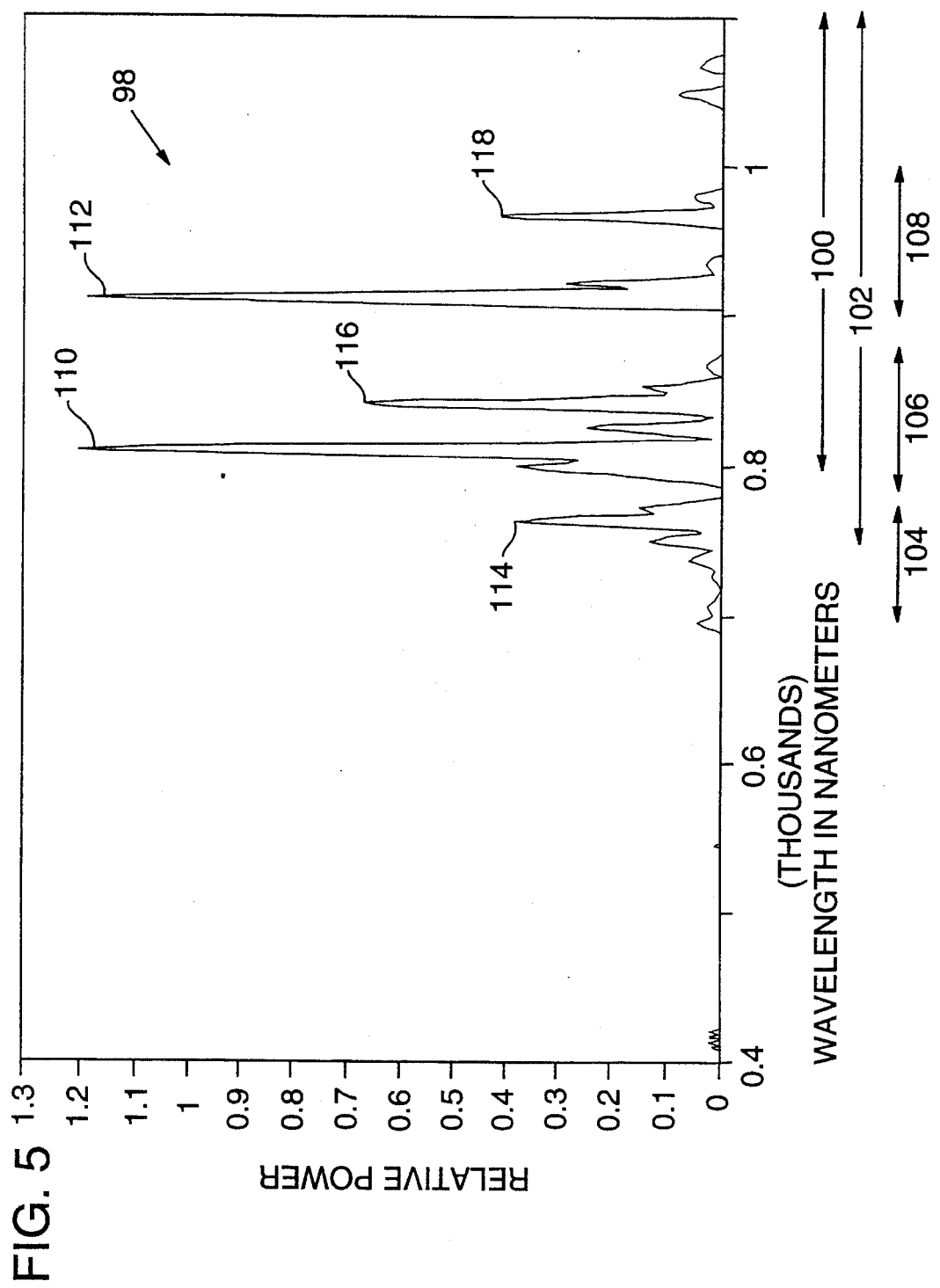

METHODS OF SEPARATING SELECTED ITEMS FROM A MIXTURE INCLUDING RAISINS AND THE SELECTED ITEMS

REFERENCE TO RELATED APPLICATION

This is a continuation of application Ser. No. 08/237,736, filed May 3, 1994, now abandoned, which is a continuation in part of U.S. patent application Ser. No. 08/063,401 of Squyres for a METHOD AND APPARATUS FOR ILLUMINATING TARGET SPECIMENS IN INSPECTION SYSTEMS, filed May 17, 1993, and assigned to the assignee of this application.

TECHNICAL FIELD

The present invention pertains to methods of operating automated optical inspection and sorting systems and, in particular, to methods for operating such systems to separate selected items from a mixture including raisins and the selected items.

BACKGROUND OF THE INVENTION

Automated optical inspection and sorting systems have been used to inspect and sort various target specimens including fruits and vegetables, processed meats, baked goods, and other foodstuffs, to separate different types of recyclable material, and to sort foreign or defective items from supplies of wood chips. These systems typically employ video cameras with charge-coupled device line scan cameras to acquire images of target specimens moved on a conveyor belt across an optical scanning area. Illumination of the specimens is generally provided by broad-spectrum tubular fluorescent lamps. Signal processing circuitry identifies variations in the shade of target specimen images and sorts target specimens accordingly.

Shipments of raisins from producers often include unwanted items such as raisin stems, leaves, and rocks. It is desirable to remove such contaminants before shipping raisins to consumers and as a check on the relative weight or volume of the unwanted items in shipments of raisins, which are usually purchased on the basis of weight and/or volume. When the raisins to be shipped to a consumer are to consist of dark raisins, it is also desirable to separate out golden raisins, which are grapes that were less mature before being picked and dried than the grapes that produce dark raisins and that are accordingly less sweet than dark raisins.

Conventional optical inspection and sorting systems using fluorescent lamps have not been used commercially to sort unwanted contaminants, e.g., grape stems and rocks, from a mixture including raisins and the contaminants because such systems cannot sort those contaminants from the mixture with sufficient accuracy to be commercially feasible.

One automated optical inspection system, the Elbiscan 5000 Laser system sold by Elbicon N. V., is effective for sorting rocks from a mixture including raisins and rocks. Its specifications indicate that it uses one or two lasers producing emissions in the red or in both the red and the green portions of the electromagnetic spectrum.

SUMMARY OF THE INVENTION

An object of the present invention is, therefore, to provide a method of operating an automated optical inspection and sorting system so that it can effectively sort grape stems from a mixture including raisins and grape stems.

Another object is to provide a method of operating an automated optical inspection and sorting system so that it can effectively sort rocks from a mixture of raisins, rocks, and grape stems while also effectively sorting the grape stems from the mixture.

A further object of this invention is to provide a method of operating an automated optical inspection and sorting system so that it can effectively sort other items commonly found mixed with raisins from the mixture.

According to the present invention, an automated optical inspection and sorting system utilizes differences in reflectivity, at wavelengths in the near infrared portion of the electromagnetic spectrum, of raisins and selected items, e.g., grape stems, rocks, leaves, and other items sometimes present in raisin shipments, to identify the selected items and to sort them from the mixture. Such a system is operated by illuminating a mixture of raisins and the selected items with illumination in the near infrared, using that illumination to identify the objects, and sorting the objects from the mixture based on that identification. The illumination has a spectral power distribution in the near infrared that is effective for the identification and sorting of the selected items in view of the reflectivities in the near infrared of the selected items and the raisins and in view of the spectral sensitivity of the camera used to identify the selected items. The system may operate by detecting reflections of the illumination, by resolving the selected items and the raisins with the illumination, or by resolving at least one part of each of the raisins and the selected items and assigning one of plural brightness values to that resolved part based on the power of the illumination detected for that part.

Additional objects and advantages of the present invention will be apparent from the following detailed description of preferred methods, which proceeds with reference to the accompanying drawings.

BRIEF DESCRIPTION OF DRAWINGS

FIG. 4 shows representative reflectivities of raisins, raisin stems, and rocks, and the relative spectral power distribution of a gas discharge lamp of the type shown in FIG. 3 and containing xenon, over a wavelength range of from about 400 to about 1100 nanometers (nm).

FIG. 5 shows the relative spectral power distribution of a gas discharge lamp of the type shown in FIG. 3 and containing argon, over the wavelength range of FIG. 4.

DETAILED DESCRIPTION OF PREFERRED METHODS

Figure 1:
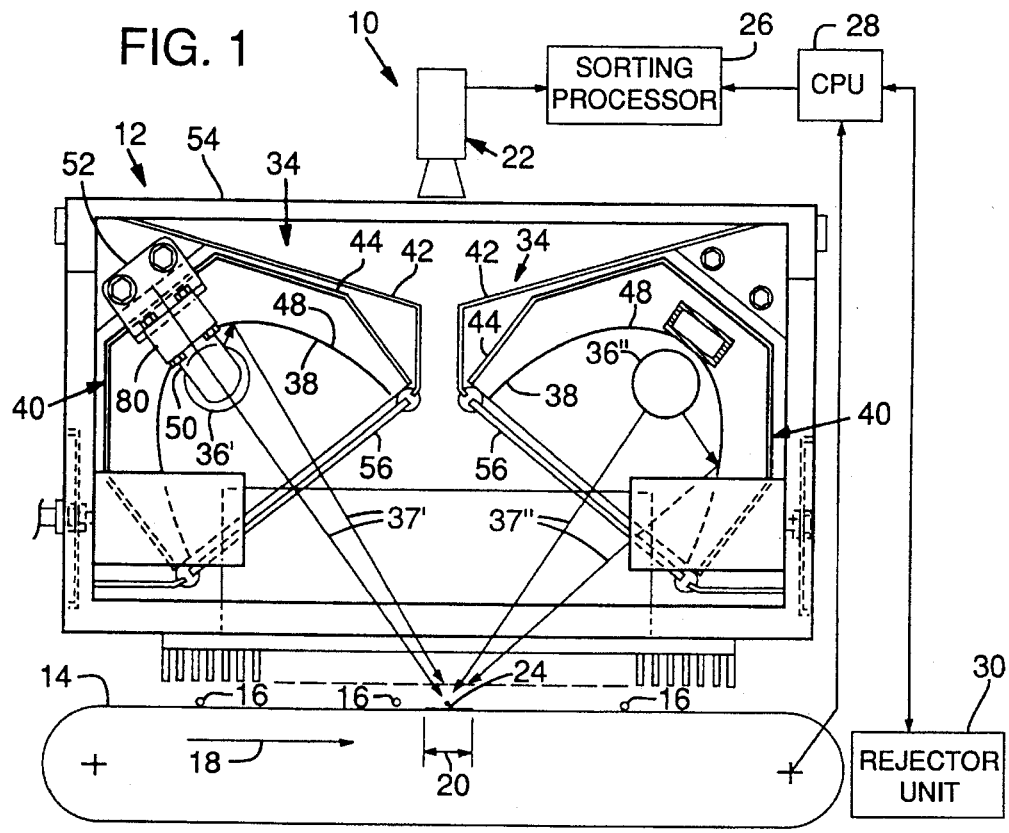
FIG. 1 is a schematic diagram showing a side elevation view of an illustrative optical inspection system operable in accordance with the present invention.
Figure 2:
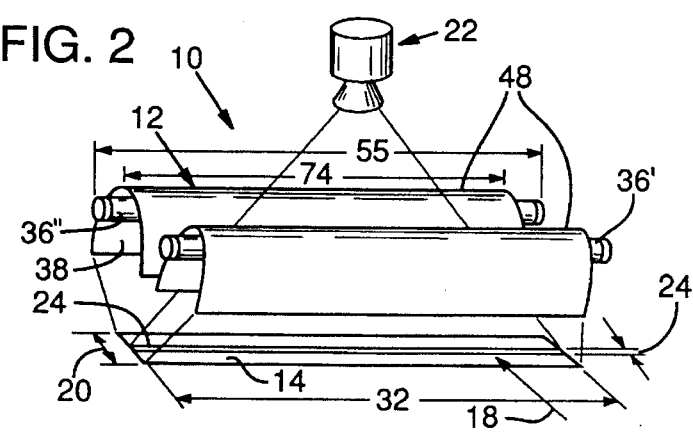
FIG. 2 is a front elevation view of the illumination system shown in FIG. 1, with parts removed for clarity.

FIGS. 1 and 2 show an illustrative automated optical inspection system 10 suitable for carrying out a method according to the invention and incorporating an illumination system 12. Inspection system 10 may be of the specimen inspection and sorting type described in U.S. Pat. Nos. 4,738,175 to Little et al. for a DEFECT DETECTION SYSTEM and 5,085,325 to Jones et al. for a COLOR SORTING SYSTEM AND METHOD, both assigned to the assignee of the instant application and incorporated herein by reference. Inspection system 10 is shown as an on-belt inspection system; the methods of the invention are also applicable in off-belt systems using in-the-air inspection.

Inspection system 10 employs an endless conveyor belt 14 having a width of about 1.2 meters (48 inches) to move target specimens 16 as quickly as 500–600 feet per minute in a direction 18 across an illumination area 20. Specimens 16 are items in a mixture that is predominantly raisins but also may include grape stems and rocks, leaves, and/or other contaminants. A high-resolution panchromatic line scan video camera 22 scans specimens 16 as they pass through a scanning area 24 within illumination area 20. Camera 22 uses a lens having a focal length that images the width across belt 14 of image scanning area 24 onto the full width of its pixel array. Camera 22 uses a silicon detector that is compatible with other system parameters such as belt speed and illumination intensity and that provides 2048 pixels; it thus resolves a distance of about 0.6 mm (about 0.023 inch) across belt 14 into one pixel and resolves into three pixels a typical width of a grape stem lying on belt 14 parallel to movement direction 18. Its pixel array is scanned once each millisecond. Camera 22 may include more than one unit; e.g., it may be two lower-resolution (1024 pixel) cameras mounted side by side.

Images of target specimens 16 are acquired by video camera 22. Camera 22 integrates the intensity of illumination received from specimens 16 to produce for each pixel in each scan one of plural brightness values or gray scale values that is determined by the spectral power distribution of the illumination, the spectral response of specimens 16, and the spectral response of camera 22. A sorting processor 26 processes image data generated by video camera 22 and arranged in image frames containing any desired number of scan lines. A central processor unit 28 linked with sorting processor 26, conveyor belt 14, and a rejector unit 30 synchronizes the timing of the position of target specimens 16 with the operation of rejector unit 30. Rejector unit 30 sorts and separates specimens 16 when sorting processor 26 determines that they include certain selected physical features such as spectral reflectance or absorption or size.

The selected physical features form the basis for sorting decisions and are characterized by the optical response of specimens 16 including recognizable patterns of reflection and absorption of radiation. The optical response of a target specimen to radiation of a particular wavelength or range of wavelengths, including any recognizable patterns of reflection and absorption of the particular wavelength or range of wavelengths of radiation, can signify defects such as the presence of grape stems among raisins.

Illumination system 12 includes multiple, e.g., two, light source assemblies 34 positioned to project electromagnetic radiation or illumination across the width of belt 14 at scanning area 24 in illumination area 20. Each light source assembly 34 includes one of two nonfluorescing rare gas discharge lamps 36' and 36" for emitting respective high-intensity illuminations 37' and 37" of select wavelengths that reflect off an inner light-reflecting surface 38 of a shroud-like reflector structure 40 and are directed toward illumination area 20. Illuminations 37' and 37" have spectral power distributions shown in a respective one of FIGS. 4–5. Lamps 36' and 36" are cooled by forced air.

Each of lamps 36' and 36" contains a rare or noble gas or a mixture of rare gases. Each rare gas and each mixture of rare gases emits select wavelengths of high-intensity illumination when ionized at the breakdown voltage. Lamps 36' and 36" emit respective illuminations 37' and 37" with an intensity approximately two to three or more times that of conventional fluorescent sources. The intensity of illuminations 37' and 37" reflecting from target specimens 16 depends on the distance between a respective one of lamps 36' and 36" and target specimens 16. Lamp 36' contains 100 percent xenon or a mixture of about 50 per unit xenon and about 50 percent neon. Lamp 36" contains 100 percent argon or a mixture of about 75 percent argon and about 25 percent neon. Lamps 36' and 36" are filled to a pressure of 665 Pa (Newtons per square meter) (approximately 5 Torr). Particular distances between each of lamps 36' and 36" and target specimens 16 are chosen according to the specific intended application of inspection and sorting system 10.

Reflector structure 40, which fits within and is supported by an outer covering 42 of light source assembly 34, includes a housing 44 and a preferably hemi-elliptical reflector 48 secured within housing 44. Each of lamps 36' and 36" may be held in place by, for example, a pair of tube sockets 50 that are supported by a light source support member 52 connected to frame 54. The length 55 of each of lamps 36' and 36" is generally a function of and typically greater than length 32 of scanning area 24.

Each of lamps 36' and 36" is positioned within rectangular frame 54 so that it lies in a direction generally perpendicular to conveyor belt travel direction 18 to illuminate target specimens 16 as they are scanned by video camera 22. Illuminations 37' and 37" propagate directly toward illumination area 20. Illuminations 37' and 37" also propagate toward and reflect from light-reflecting surface 38 of hemi-elliptical reflector 48 toward illumination area 20. Hemi-elliptical reflectors 48 have lengths 74 that are about equal to length 32 of scanning area 24 and about equal to or shorter than length 55 of lamps 36' and 36". Because reflectors 48 are of hemi-elliptical shape, reflectors 48 produce a line focus of illuminations 37' and 37" that strikes illumination area 20 and scanning area 24 on conveyor belt 14.

Lamps 36' and 36" also typically have a smaller diameter than conventional broad-spectrum fluorescent tubes. When used with hemi-elliptical reflectors, smaller diameter lamps come closer to approximating a line source of illumination than larger diameter lamps. Line sources are more efficient than diffuse sources of illumination.

Preferably, an optically transmissive protective covering 56 encloses reflector structure 40 to protect target specimens 16 from debris falling from a broken lamp 36' or 36". Also, hemi-elliptical reflector 48 supports a preformed aluminum substrate that carries on its inner surface 38 a light-reflective coating such as, for example, the "BV2 coating" having 89 to 93 percent reflectivity, which is produced by Optical Coating Labs, Inc. of Santa Rosa, Calif.

Figure 3:
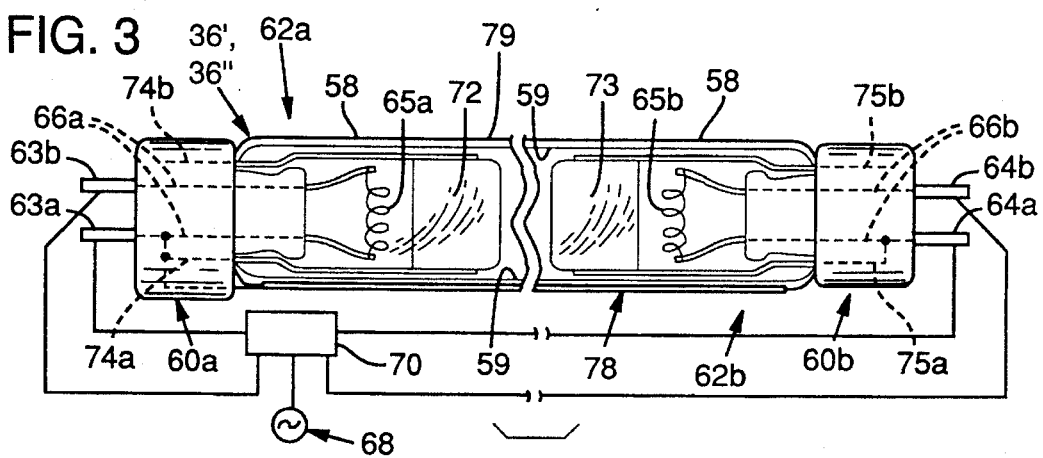
FIG. 3 is a simplified side view of a rare gas discharge lamp of a type used in practicing the present invention, with associated electrical components shown schematically.

Referring to FIG. 3, each of lamps 36' and 36" comprises a light-transmitting, gas-impervious tubular outer envelope 58, which may be of generally round, oblong, ovoid, figure-eight, or other cross-section, shape, or configuration and is formed preferably of hard or soft optically transmissive glass or quartz. In one preferred embodiment, outer envelope 58 is approximately 175 cm (centimeters) in length and has an outer diameter of approximately 20 mm (millimeters) with walls 1.6 mm thick. Envelope 58 is filled with the gas mixtures described above for lamps 37' and 37" or with any other mixture of one or more of the rare or noble gases such as neon, argon, xenon, krypton, or helium that is effective to produce illumination with a suitable spectral power distribution and with sufficiently high intensity, following procedures known in the art such as are described in "Neon Techniques and Handling" by Samuel C. Miller (1990) available from Sign-of-the-Times Publishing Co., 407 Gilbert Avenue, Cincinnati, Ohio 45202. Lamps 36' and 36" are preferably formed without a phosphor layer or layer of other absorbent or fluorescent material on inner surface 59 of light-transmitting tubular outer envelope 58.

Secured to opposed ends of outer envelope 58 are bases 60a and 60b. Bases 60a and 60b extend between electrode structures 62a and 62b respectively and pairs of pins 63 and 64, respectively. Lamp socket 50 (FIG. 1) provides electrical energy to lamp 36' or 36" through respective pairs of pins 63 and 64. In one preferred embodiment, electrode structures 62a and 62b are model HI 800 MA electrodes available from EGL in Newark, N.J. Electrode filaments 65a and 65b are connected to respective pairs of pins 63 and 64 by respective pairs of filament electrode leads 66a and 66b.

Lamps 36' and 36" are excited by means of the application of a voltage between electrode filaments 65a and 65b. Current flows between filaments 65a and 65b after a certain acceptable potential, or breakdown voltage, is applied between filaments 65a and 65b by light source driver 68 through ballast 70. The rare or noble discharge gas creates an electrically conductive path between filaments 65a and 65b when the gas ionizes at the breakdown voltage. Ballast 70 transforms the external source of alternating current to the voltage level necessary to operate rare gas discharge lamp 36. Filaments 65a and 65b are each connected by way of respective pair of filaments leads 66a and 66b to ballast 70 and light source driver 68. Ballast 70 converts 115-volt commercial voltage into a high starting voltage, current-limited lower operating voltages, and heater voltages. Examples of voltages are a starting voltage of approximately 2500 volts DC, an operating voltage of from approximately 400 to 1000 volts at approximately 50 KHz with a current of approximately 50 milliamps to 1000 milliamps, and a heater voltage of approximately 6 volts, also at approximately 50 KHz. Ballast 70 is preferably model 16144-2 available from Mercron of Richardson, Tex., which is a photocell feedback circuit that monitors the average light output of lamps 36' or 36" and that is operable to automatically boost or reduce the drive current to maintain a constant output of illumination 37' or 37".

Bombardment electrode 72 includes pair of bombardment electrode leads 74a and 74b; bombardment electrode 73 includes pair of bombardment electrode leads 75a and 75b. Bombardment electrode leads 74a and 75a are electrically connected through light source driver 68 and ballast 70. Bombardment electrodes 72 and 73 remove impurities from rare gas discharge lamp 36 prior to realtime operation by high voltage discharge. During realtime operation bombardment electrodes 72 and 73 contribute to the ionization of the discharge gas. Alternately, impurities may be removed from light-transmitting tubular outer envelope 58 by baking at elevated temperatures, e.g., 500° C., under a vacuum prior to filling with rare or noble gases.

An electrically conductive film ground plane 78 adheres to the outer surface 79 of light-transmitting outer envelope 58 and extends substantially the full length of outer envelope 58. Ground plane 78 is electrically connected to bombardment electrode lead 74a. Ground plane 78 is preferably approximately 15 mm wide and constructed of aluminum foil or other suitable material. Ground plane 78 serves to facilitate ionization of the discharge gas and allows activation of rare gas discharge lamp 36 at a significantly lower voltage than would be possible otherwise.

Each of lamps 36' and 36" plugs into tube socket 50 of lamp fixture 80 designed to support it and to supply electric current to electrode filaments 65a and 65b and to bombardment electrodes 72 and 73. Lamp fixture 80 may include ballast 70.

FIG. 4 shows representative reflectivities of raisins (curve 80), grape stems (curve 82), and rocks (curve 84) over a range of wavelengths of electromagnetic radiation.

Most human eyes can detect electromagnetic radiation in a spectral range of about 380 to about 750 nm but cannot detect electromagnetic radiation in the infrared spectral range. Electromagnetic radiation in the near infrared spectral range includes wavelengths of from about 750 to about 1100 nm.

Over most of the visible wavelength range (i.e., from about 400 to about 710 nm) raisins and rocks have very similar reflectivities. However, at wavelengths beginning in the far red and extending into the near infrared (e.g., from about 710 to about 1100 nm), rocks have lower reflectivity than raisins. At blue, green, and yellow wavelengths (e.g., from about 400 to about 580 nm), grape stems have a somewhat higher reflectivity than raisins. However, beginning at orange wavelengths (e.g., about 600 nm), grape stems begin to have a significantly higher reflectivity than raisins; that higher reflectivity is especially pronounced in the near infrared up to about 1100 nm. Although not shown in FIG. 4, leaves, e.g., grape leaves, also have a much higher reflectivity than raisins at wavelengths in the near infrared.

As a practical matter, automated optical inspection systems best distinguish grape stems or other selected items from raisins when their reflectivities differ by as much as possible. Grape stems and raisins in a single shipment typically have variations in reflectivity that make it impractical to sort them with commercially-acceptable accuracy when their reflectivities are too close. At wavelengths in the near infrared, particularly at wavelengths between about 800 and about 1100 nm, raisins and grape stems have a particularly large difference in reflectivity. When viewed with illumination in the near infrared, grape stems are so highly reflective that they appear like mirrors in comparison to raisins.

The invention exploits those differences in reflectivity by illuminating a mixture of raisins and selected items with illumination in the near infrared and using that illumination to identify the selected items in the mixture and to decide whether to sort them from the mixture. Items that may be separated from the mixture include those that reflect more of the power of the illumination in the near infrared than do the raisins, e.g., vegetable matter that contains chlorophyll, grape leaves, and/or grape stems (e.g., loose grape stems, grape stems attached to raisins (cap stems), or grape stems embedded in raisins), and those that reflect less of the power of the illumination in the near infrared than do the raisins, e.g., rocks. Other items that may be separated from the mixture include different types of raisins, e.g., golden raisins may be separated from a mixture that is predominantly dark raisins.

A first method of making such a separation illuminates mixture 16 with illumination characterized by a spectral power distribution including wavelengths in the near infrared. Reflections of wavelengths of the illumination in the near infrared from the mixture are detected, and the selected items in the mixture are identified based on the detected reflections. The selected items are separated from the mixture with use of the identification. This method directly exploits the differences in reflectivity in the near infrared by using reflections.

A second method illuminates the mixture with illumination in the near infrared characterized by a spectral power distribution. The selected items in the mixture are resolved and identified with the illumination and separated from the mixture with use of the identification. Resolving the selected items assists in identifying and separating them. If the selected items are not resolved, the only way to separate them from the mixture is to separate the raisins, which places impractical demands on rejector unit 30 (FIG. 1).

Successfully resolving selected items such as grape stems depends on several factors. The illumination provided to such items must be of sufficiently high intensity to allow camera 22 with its particular speed, and sorting processor 26 and CPU 28 with their bandwidth, to form an image of and to evaluate the item in the time available in view of the motion of the item on belt 14. Resolving items smaller than raisins requires more intense illumination, a faster speed of camera 22, and/or a slower speed of belt 14 than is required for resolving raisins. Skilled persons are able to adjust the foregoing factors to make an operable system to carry out a method according to the invention. The spectral energy distribution of illuminations 37' and 37" facilitates resolving grape stems by concentrating the energy with which items 16 are illuminated in ranges of wavelengths in which the reflectivities of raisins and grape stems have their greatest differences.

A third method illuminates mixture 16 with illumination in the near infrared characterized by a spectral power distribution having a wavelength range. At least a part of each of the raisins and the selected items in the mixture is resolved with the illumination. One of plural brightness values is determined for at least one resolved part of each of the raisins and the selected items; the brightness value is indicative of an integration over a significant part of the wavelength range of the intensity of the illumination resolved for that part. The selected items are separated from mixture 16 with the use of the brightness values.

The brightness values are preferably one of a range of gray scale values. The resolved part of each of the raisins and the selected items is resolved in one, two, or three pixels, each of which is assigned one of the brightness values. Grape stems are of small size relative to raisins and must be resolved to be identified and sorted effectively. Resolving grape stems in two pixels provides better resolution and identification than resolving them in one pixel; resolving grape stems in three pixels provides even better resolution and identification and permits more accurate determination of the orientation of the grape stems, which facilitates accurate sorting of the grape stems from mixture 16.

The third method is particularly useful in identifying grape stems embedded in raisins. Raisins are somewhat translucent to illumination at wavelengths in the near infrared. The high reflectivity of grape stems relative to raisins in the near infrared thus permits resolution and identification of a grape stem even when it is embedded in a raisin. Resolving such an embedded grape stem facilitates separating the raisin with its embedded or covered grape stem from the mixture. Because raisins may not be sufficiently translucent, identifying nearly all grape stems embedded in raisins may require in-air illumination and inspection, which is familiar to skilled persons.

When inspection system 10 is used to separate selected items from a mixture 16 including raisins and the selected items, lamps 36' and 36" are designed to emit electromagnetic radiation characterized by a spectral power distribution over a wavelength range that produces good results in distinguishing the raisins from the selected items with video camera 22. The lamps are preferably chosen and operated to provide a total energy flux in scanning area 24 (FIGS. 1–2) sufficient for the operation of camera 22. Lamps 36' and 36" may both be the same type of rare gas discharge lamp. However, a wider range of separation capabilities is achieved by selecting as one of the lamps a first type of lamp characterized by a first spectral power distribution that distinguishes raisins from a first type of unwanted item in mixture 16 and by selecting as another of the lamps a second type of lamp characterized by a second spectral power distribution that better distinguishes raisins from a second type of unwanted item in mixture 16. An automated optical inspection system sold by Simco/Ramic Corp. of Medford, Oreg., the assignee of this application, uses two lamps 36' containing 100 percent xenon and one lamp 36" containing 100 percent argon to achieve an energy flux of about 25 milliwatts/cm$^2$ across belt 14 in scanning area 24.

Lamp 36' produces illumination that is particularly effective in separating raisin stems from a mixture that is predominantly raisins; FIG. 4 shows the relative spectral power distribution 86 of a lamp 36' containing 100 percent xenon. Substantially all the power in spectral power distribution 86 is at wavelengths in the near infrared, specifically, at wavelengths in respective spectral ranges 88 of between about 800 to about 1100 nm and 90 of from about 800 to about 1000 nm. Within spectral ranges 88 and 90, the power is broadly distributed over several different wavelength ranges. A significant fraction of the total power is in a spectral range 92 of from about 850 to about 950 nm. A significant fraction of the total power is also in each of two nonoverlapping continuous spectral ranges 94 and 96 having respective ranges from about 800 to about 850 and from about 950 to about 1000 nm. Each of ranges 94 and 96 includes a wavelength range of about 50 nm, and each is separated by about 100 nm.

Lamp 36" produces illumination that is particularly effective in separating golden raisins from a mixture that is predominantly dark raisins; FIG. 5 shows the relative spectral power distribution 98 of a lamp 36" containing 100 percent argon. Substantially all the power in spectral power distribution 98 is at wavelengths in the near infrared, specifically, at wavelengths in respective spectral ranges 100 of between about 800 and about 1100 nm and 102 of from about 750 to about 1100 nm. Within or extending slightly beyond those spectral ranges, the power is distributed over several different wavelength ranges. A significant fraction of the total power in the illumination is in each of three nonoverlapping continuous spectral ranges 104 from about 690 to about 780 nm, 106 from about 790 nm to about 870 nm, and 108 from about 900 to about 990 nm. Each of those ranges includes a wavelength range of about 90 nm. A significant fraction of the total power in the illumination is in ranges 104 and 108, which are nonoverlapping, continuous, and separated by at least about 100 nm. Spectral power distribution 98 also has first and second highest peaks 110 and 112 separated by at least about 100 nm and three peaks 114, 116, and 118 of intermediate height separated by at least about 80 nm.

Although lamps 36' and 36" are preferred sources of the illumination, other sources of illumination in the near infrared can also be effective. Gas discharge lamps with other gas mixtures could be used. Instead of or in addition to gas discharge lamps, the illumination could be provided by one or more lasers. GaAs lasers produce high-intensity emission at about 904 nm and can be tuned to produce emissions at other wavelengths in the near infrared by varying the trapping levels with additions of suitable phosphors; such lasers would be especially useful with a camera 22 that used a silicon detector. Nd:YAG (neodymium:yttrium-aluminum-garnet) lasers produce high-intensity emission at about 1064 nm.

Moreover, sources that produce illumination not only in the near infrared but also in other wavelength ranges can also be effective sources of the illumination when those sources provide illumination with sufficient intensity in the near infrared and when any illumination from those sources in .wavelength ranges outside the near infrared does not interfere with the use of the near infrared wavelengths in a method according to the invention. As examples, wavelengths outside the near infrared could be filtered from the illumination from a source before or after the illumination reaches mixture 16, or camera 22 could be selected to have sufficiently small response to wavelengths outside the near infrared to allow sorting actions to be carried out primarily on the basis of illumination at wavelengths in the near infrared (i.e., the spectral response characteristics of camera 22 could act as a filter). For reasons of efficiency and of avoiding non-functional illumination of belt 14 and mixture 16, the illumination is preferably concentrated in a range of wavelengths that is effective in performing a method according to the invention. Preferably the overall response of system 10 in identifying and sorting selected items from mixture 16 is based on illumination received from mixture 16 in a wavelength range or ranges where the difference between the integrated responses of system 10 to raisins and to the selected items over the wavelength range of the spectral power distribution of the illumination (i.e., the separation index) is unambiguous and at or near a high or its maximum value.

Whatever the source used to produce the illumination, the effectiveness of the methods of separating selected items from mixture 16 including raisins and the selected items depends on the effect in combination of the intensity of the illumination, the spectral power distribution of the illumination, the difference in reflectivities of the raisins and the selected items over the wavelength range encompassing the spectral energy distribution, the sensitivity of camera 22 over that wavelength range, and the bandwidth of processor 26 and CPU 28. Those factors are balanced to optimize the effectiveness of system 10 in identifying and sorting from mixture 16 the selected items to be removed from the mixture.

The spectral energy distribution of the illumination may be different from that of lamps 36' and 36". A silicon detector, which is preferably used in camera 22, has maximum response at about 750 nm and substantially reduced response at about 400 nm and about 1100 nm. For some systems in some applications, illumination in or including the orange to red portion of the electromagnetic spectrum, e.g., having wavelengths of from about 600 to about 750 nm, from about 650 to about 750 nm, or from about 700 to about 750 nm, may be effective in sorting grape stems from mixture 16.

Figure 6A:
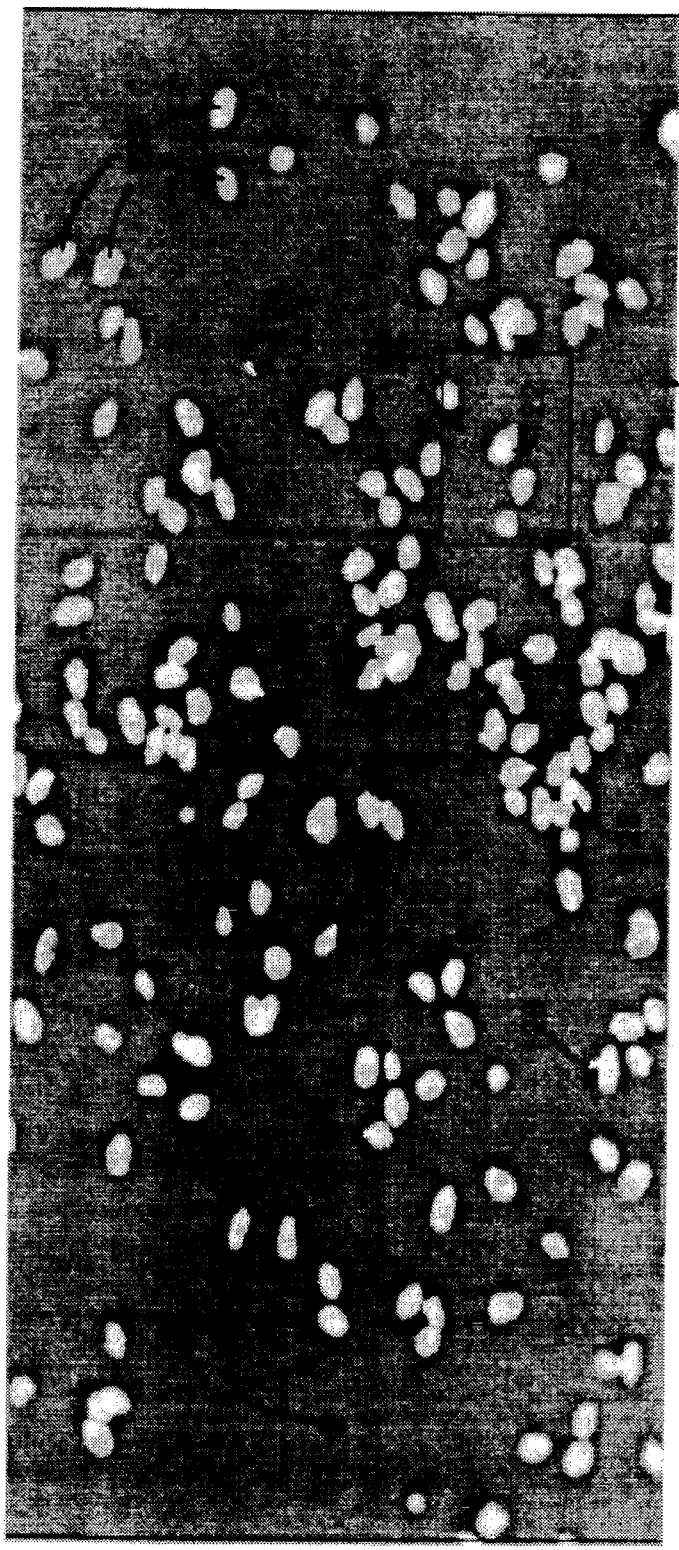
FIG. 6A shows brightness values assigned to golden raisins, raisin stems (including a loose stem, cap stems, and an embedded stem) and a leaf in an automated optical inspection system carrying out a method according to the invention.

A method according to the invention produces good results in sorting grape stems, leaves, and rocks from a mixture that is predominantly raisins. FIG. 6A is a screen dump from a Simco/Ramic automated optical inspection system using two lamps 36' with 100 percent xenon and one lamp 36" with 100 percent argon that had viewed a mixture 16 of golden raisins 120 of a type sold as golden raisins, a grape leaf 122, and grape stems distributed on the surface of a conveyor belt. Grape stems include a loose stem 124, cap stems 126, and an embedded stem 128.

Figure 6B:
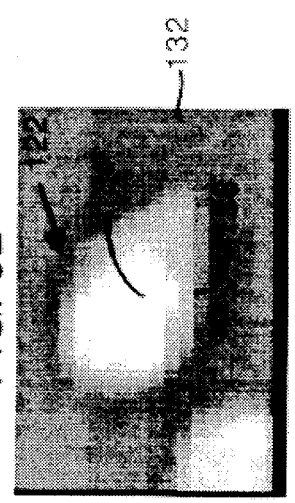
FIG. 6B is a detailed view of the leaf shown in FIG. 6A.

Main view 130 shows different gray scale brightness values assigned by that system 10 to golden raisins 120, grape leaf 122, and stems 124, 126, and 128. The stems and the leaf are readily distinguishable from the raisins on the basis of the brightness values. The resolution provided by camera 22 is more than adequate to identify stems and their orientations. FIG. 6B is a detailed view 132 of leaf 122 and illustrates the resolution of the system in distinguishing regions 134 of the leaf that reflected more of the power in the illumination than other regions 136. This assists in distinguishing a leaf or a stem for separation from mixture 16.

It will be obvious to those having skill in the art that many changes may be made in the above-described details of the present invention without departing from the underlying principles thereof. In addition, many changes may be made to the details of a system for carrying out a method in accordance with the present invention. For example, illumination system 12 may also comprise multiple video cameras 22, a single light source 36 and hemi-elliptical reflector 48, and light source or sources 36 at various distances and angles from conveyor belt 14. The scope of the present invention, therefore, should be determined only by the following claims.

We claim:

1. A method of operating an automated optical inspection system to separate selected items from a mixture including raisins and the selected items, comprising:

illuminating the mixture with illumination characterized by a spectral power distribution including a high intensity of power at wavelengths in the near infrared;

detecting reflections of wavelengths of the illumination in the near infrared from the mixture;

identifying the selected items in the mixture based on the detected reflections; and separating the selected items from the mixture with use of the identification.

2. The method of claim 1, wherein substantially all of the power in the illumination is contained in wavelengths in the near infrared.

3. The method of claim 1, wherein the selected items reflect more of the power of the illumination in the near infrared than do the raisins.

4. The method of claim 1, wherein the selected items include one or more of vegetable matter containing chlorophyll, grape leaves, loose grape stems, grape stems attached to raisins, and grape stems embedded in raisins.

5. The method of claim 1, wherein the selected items reflect less of the power of the illumination in the near infrared than do the raisins.

6. The method of claim 1, wherein the selected items comprise rocks.

7. The method of claim 1, wherein the raisins comprise dark raisins, and the selected items comprise golden raisins.

8. The method of claim 1, further comprising producing the illumination with a laser.

9. A method of operating an automated optical inspection system to separate selected items from a mixture including raisins and the selected items, comprising:

illuminating the mixture with high-intensity illumination in the near infrared characterized by a spectral power distribution;

resolving with the illumination selected items in the mixture;

identifying the resolved selected items with the illumination; and separating the resolved selected items from the mixture with use of the identification.

10. The method of claim 9, wherein substantially all of the power in the illumination is at wavelengths within a spectral range of from about 800 to about 1100 nm.

11. The method of claim 9, wherein substantially all of the power in the illumination is at wavelengths within a spectral range of from about 800 to about 1000 nm.

12. The method of claim 9, wherein a significant fraction of the total power in the illumination is in a spectral range of from about 850 to about 950 nm.

13. The method of claim 9, wherein a significant fraction of the total power in the illumination is in each of two nonoverlapping continuous spectral ranges, each including a wavelength range of about 50 nm.

14. The method of claim 9, wherein substantially all of the power in the illumination is at wavelengths within a spectral range of from about 750 to about 1100 nm.

15. The method of claim 9, wherein a significant fraction of the total power in the illumination is in each of two nonoverlapping continuous spectral ranges, each including a wavelength range of about 90 nm.

16. The method of claim 15, wherein the two spectral ranges are from about 790 to about 870 nm and from about 900 to about 990 nm.

17. The method of claim 9, further comprising producing the illumination with a laser.

18. A method of operating an automated optical inspection system to separate selected items from a mixture including raisins and the selected items, comprising:

illuminating the mixture with high-intensity illumination in the near infrared characterized by a spectral power distribution having a wavelength range;

resolving with the illumination at least a part of each of the raisins and the selected items in the mixture;

determining for at least one resolved part of each of the raisins and the selected items one of plural brightness values indicative of an integration over a significant part of the wavelength range of the intensity of the illumination resolved for that part; and separating the selected items from the mixture with the use of the brightness values.

19. The method of claim 18, wherein the selected items comprise raisin stems embedded in raisins.

20. The method of claim 18, wherein resolving with the illumination at least a part of each of the raisins and the selected items comprises resolving in at least one pixel each of the raisins and the selected items.

21. The method of claim 18, wherein resolving with the illumination at least a part of each of the raisins and the selected items comprises resolving in at least two pixels each of the raisins and the selected items.

22. The method of claim 18, wherein resolving with the illumination at least a part of each of the raisins and the selected items comprises resolving in at least three pixels each of the raisins and the selected items.

23. The method of claim 18, further comprising producing the illumination with a laser.

24. A method of operating an automated optical inspection system to separate grape stems from a mixture including raisins and the grape stems, comprising:

illuminating the mixture with high-intensity illumination in a wavelength range of from about 600 to about 1100 nm;

resolving the grape stems with the illumination;

identifying the grape stems with the illumination; and separating the grape stems from the mixture with use of the identification.

25. The method of claim 24, wherein identifying the grape stems comprises identifying the grape stems with reflections of the illumination.

26. The method of claim 24, wherein:

resolving the grape stems comprises resolving with the illumination at least a part of each of the raisins and the grape stems;

identifying the grape stems comprises determining for at least one resolved part of the raisins and the grape stems one of plural brightness values indicative of an integration over a significant part of the wavelength range of the intensity of the illumination resolved for that part; and separating the grape stems from the mixture comprises separating the grape stems from the mixture with use of the brightness values.

27. The method of claim 26, wherein resolving the grape stems comprises resolving in at least one pixel each of the raisins and the grape stems.

* * * * *